(12) United States Patent
Adawi et al.

(10) Patent No.: US 11,633,228 B2
(45) Date of Patent: Apr. 25, 2023

(54) IDENTIFYING PULMONARY VEIN OCCLUSION BY DIMENSION DEFORMATIONS OF BALLOON CATHETER

(71) Applicant: Biosense Webster (Israel) Ltd., Yokneam (IL)

(72) Inventors: Eid Adawi, Tur'an (IL); Zvi Dekel, Zichron Yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 756 days.

(21) Appl. No.: 16/593,246

(22) Filed: Oct. 4, 2019

(65) Prior Publication Data

US 2021/0100611 A1    Apr. 8, 2021

(51) Int. Cl.
| | |
|---|---|
| *A61B 18/00* | (2006.01) |
| *A61B 18/14* | (2006.01) |
| *A61B 5/00* | (2006.01) |
| *A61B 5/06* | (2006.01) |

(52) U.S. Cl.
CPC .......... *A61B 18/1492* (2013.01); *A61B 5/065* (2013.01); *A61B 5/6853* (2013.01); *A61B 2018/0022* (2013.01); *A61B 2018/00577* (2013.01)

(58) Field of Classification Search
CPC .......... A61B 2018/00577; A61B 2018/00244; A61B 2018/0022; A61B 5/065; A61B 5/6853; A61B 18/1492
See application file for complete search history.

(56) References Cited

U.S. PATENT DOCUMENTS

| | | |
|---|---|---|
| 5,391,199 A | 2/1995 | Ben-Haim |
| 5,795,325 A | 8/1998 | Valley et al. |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 7,756,576 B2 | 7/2010 | Levin |

(Continued)

FOREIGN PATENT DOCUMENTS

| | | |
|---|---|---|
| WO | WO 96/05768 A1 | 2/1996 |
| WO | 2013022853 A1 | 2/2013 |

OTHER PUBLICATIONS

Extended European Search Report issued in European Patent Application No. 20 19 9789.

*Primary Examiner* — Linda C Dvorak
*Assistant Examiner* — Nicholas S Borsch
(74) *Attorney, Agent, or Firm* — Troutman Pepper Hamilton Sanders LLP

(57) ABSTRACT

A method includes receiving position signals that are indicative of positions of multiple electrodes disposed on an expandable balloon that is fitted at a distal end of a shaft for engaging a lumen of an organ to occlude the lumen. Based on the received position signals, a change is calculated in one or more dimensions of the balloon between (i) a first configuration in which the balloon is inflated but not engaged in the lumen, and (ii) a second configuration in which the balloon is inflated and engaged in the lumen. Using the calculated change, a degree is estimated to which the balloon occludes the lumen. The estimated degree of occlusion is presented to a user.

20 Claims, 3 Drawing Sheets

(56) References Cited

U.S. PATENT DOCUMENTS

| | | |
|---|---|---|
| 7,848,787 B2 | 12/2010 | Osadchy |
| 7,869,865 B2 | 1/2011 | Govari et al. |
| 8,456,182 B2 | 6/2013 | Bar-Tal et al. |
| 9,636,172 B2 | 5/2017 | Hu |
| 2002/0065455 A1 | 5/2002 | Ben-Haim et al. |
| 2003/0120150 A1 | 6/2003 | Govari |
| 2003/0199923 A1 | 10/2003 | Khairkhahan et al. |
| 2004/0068178 A1 | 4/2004 | Govari |
| 2009/0326526 A1* | 12/2009 | Ingle .................. A61B 18/0218 606/21 |
| 2010/0094328 A1* | 4/2010 | O'dea .................. A61M 29/02 606/192 |
| 2011/0184400 A1 | 7/2011 | Pageard |
| 2012/0143179 A1 | 6/2012 | Avitall |
| 2013/0116550 A1* | 5/2013 | Ishii .................... A61B 6/5205 600/424 |
| 2015/0223704 A1 | 8/2015 | Haverkost et al. |
| 2015/0223729 A1* | 8/2015 | Balachandran ...... A61B 5/1076 600/374 |
| 2017/0333122 A1 | 11/2017 | Rajagopalan et al. |
| 2018/0076366 A1 | 3/2018 | Halbritter et al. |

\* cited by examiner

IDENTIFYING PULMONARY VEIN OCCLUSION BY DIMENSION DEFORMATIONS OF BALLOON CATHETER

FIELD OF THE INVENTION

The present invention relates generally to tracking a medical probe inside a living body, and specifically to tracking a shape of the medical probe.

BACKGROUND OF THE INVENTION

Expandable probes for occluding a lumen in the body were previously proposed in the patent literature. For example, U.S. Pat. No. 5,795,325 describes measurement of pressure on both sides of an occluding balloon for determining when pressure forces on the balloon may cause migration of the balloon. An alarm indicates when the pressure force on the balloon exceed a predetermined threshold. In another aspect of the invention, a pressure monitor determines when a rate of pressure increase with respect to the fluid volume in the balloon reaches a predetermined threshold when inflating the occluding balloon. A predetermined amount of fluid is then added to the balloon so that the balloon is not under-inflated or over-inflated.

As another example, U.S. Patent Application Publication 2011/0184400 describes a method and system for cryogenically ablating large areas of tissue within the left atrium. In an exemplary embodiment, a cryotherapy device includes a catheter body, a proximal end and a distal end, a first lumen, a second lumen, and an ablation element expandable from a first diameter to a second diameter. The ablation element has a surface portion that conforms to the uneven surface topography of the cardiac tissue. The ablation element can include one or more deformable balloons and/or flexible elements. The surface of the balloon can further be shaped by regulation of pressure within the one or more balloons. Further, as there may be variations in the size, shape or other dimensions of the vessel being occluded, a second balloon may be selectively, controllably expanded to a fraction of its overall inflation/size capacity to obtain the resulting, desired occlusion. In an exemplary method, a tissue ablation device is provided and tissue in the left atrium is ablated with the device, whereby the ablation is created by freezing tissue.

SUMMARY OF THE INVENTION

An embodiment of the present invention provides a method including receiving position signals that are indicative of positions of multiple electrodes disposed on an expandable balloon that is fitted at a distal end of a shaft for engaging a lumen of an organ to occlude the lumen. Based on the received position signals, a change is calculated in one or more dimensions of the balloon between (i) a first configuration in which the balloon is inflated but not engaged in the lumen, and (ii) a second configuration in which the balloon is inflated and engaged in the lumen. Using the calculated change, a degree is estimated to which the balloon occludes the lumen. The estimated degree of occlusion is presented to a user.

In some embodiments, estimating the degree includes deriving a Balloon Inflation Index (BII) from the calculated change in the dimensions, and estimating the degree to which the balloon occludes the lumen based on the BII.

In some embodiments, calculating the change in dimensions includes calculating a change in a radius of the balloon.

In an embodiment, calculating the change in the radius of the balloon includes:

measuring positions of ablation electrodes disposed over the expandable balloon using Active Current Location (ACL). A circle is best fitted to the measured positions. A radius of the best fitted circle is calculated.

In another embodiment, receiving the position signals includes receiving additional position signals from one or more position sensors disposed on the distal end of the shaft, and wherein calculating the change in dimensions includes calculating a change in a length of the balloon along a longitudinal axis of the balloon based on the additional position signals.

In some embodiments, estimating the degree to which the balloon occludes the lumen includes numerically grading the degree. In other embodiments, estimating the degree to which the balloon occludes the lumen includes textually grading the degree.

In an embodiment, the lumen includes an ostium of a pulmonary vein (PV).

There is additionally provided, in accordance with an embodiment of the present invention, a system including an interface and a processor. The interface is configured to receive position signals that are indicative of positions of multiple electrodes disposed on an expandable balloon that is fitted at a distal end of a shaft for engaging a lumen of an organ to occlude the lumen. The processor is configured to (a) based on the received position signals, calculate a change in one or more dimensions of the balloon, (b) using the calculated change in dimensions, estimate a degree to which the balloon occludes the lumen, and (c) present the estimated degree of occlusion to a user.

The present invention will be more fully understood from the following detailed description of the embodiments thereof, taken together with the drawings in which:

DETAILED DESCRIPTION OF EMBODIMENTS

Overview

Figure 1:
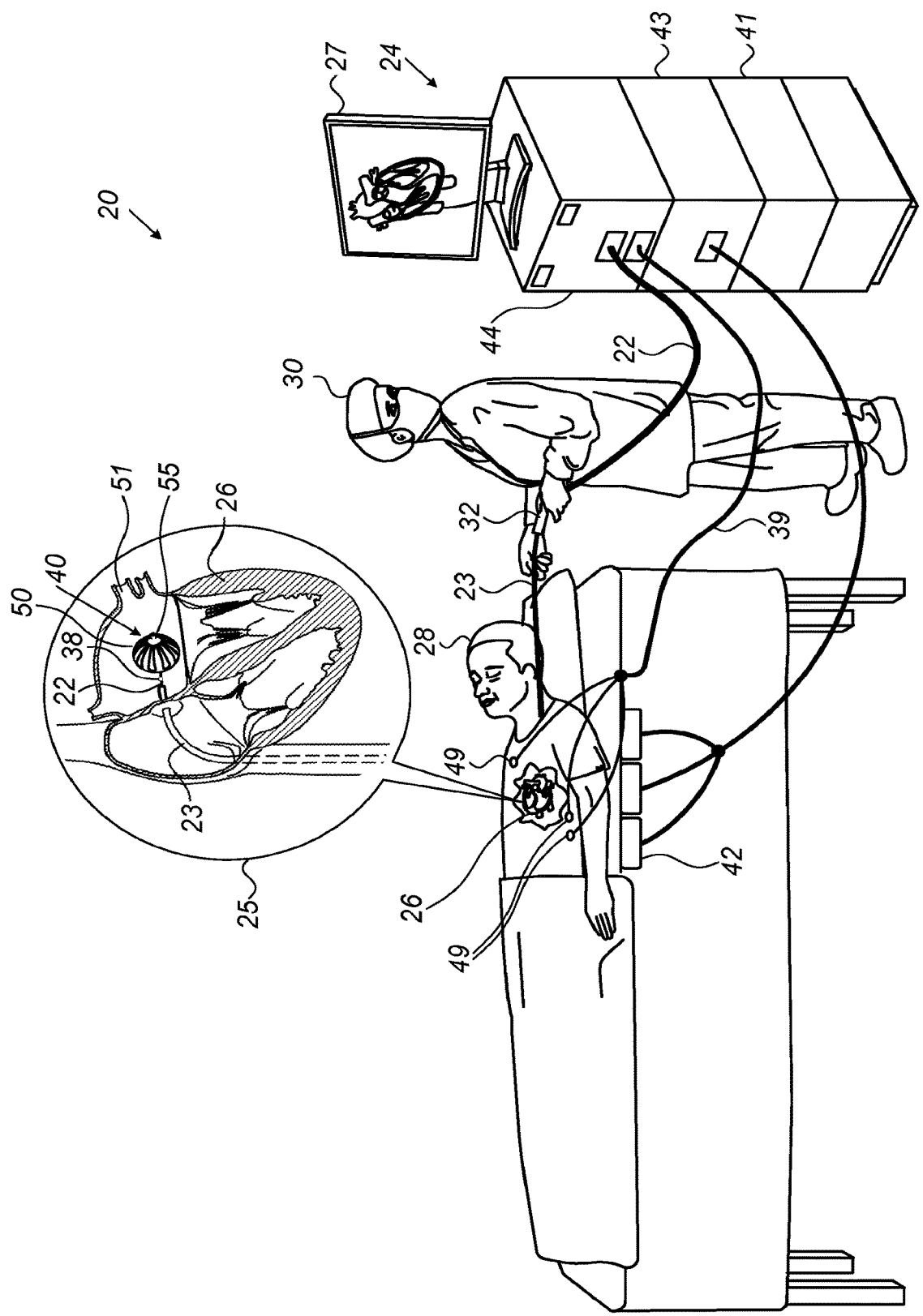
FIG. 1 is a schematic, pictorial illustration of a catheter-based position-tracking and ablation system comprising a radiofrequency (RF) ablation balloon, in accordance with an embodiment of the present invention.

For efficient ablation of tissue of a lumen using a balloon catheter, such as a radiofrequency (RF) ablation balloon catheter, it is important that the ablating electrodes disposed over the balloon membrane are in good physical contact with the tissue being ablated. For example, for a safe and effective pulmonary vein (PV) isolation, all ablation electrodes should be in good contact over a perimeter of a circularly shaped ostium of the PV. Therefore, it is important, before performing the ablation, to ensure that the balloon fully occludes the vein.

However, checking for full occlusion of a lumen, such as of a circular ostium, for example, by checking for occlusion of a distal blood vessel (e.g., of the PV), is a process that conventionally relies on another modality, such as fluoroscopy. Unfortunately, fluoroscopy (i.e., observing the behavior of an X-ray opaque contrast agent after it has been injected) may sometimes have side effects related to the contrast material itself and to the use of X-ray radiation.

Embodiments of the present invention that are described hereinafter provide improved techniques for monitoring, e.g., immediately before ablation, how well an expandable (e.g., inflatable) cardiac ablation balloon occludes a circular lumen, such as an ostium of a PV. The disclosed techniques provide systems and methods that can provide a physician with an estimated degree of occlusion by estimating a degree to which the balloon occludes the lumen. To derive the estimation, a processor calculates a change in one or more dimensions of the balloon between (i) a first configuration in which the balloon is inflated but not engaged in the lumen, and (ii) a second configuration in which the balloon is inflated and engaged in the lumen.

In some embodiments, the estimation of balloon occlusion relies on an estimated degree of balloon inflation while the balloon is pressed against a wall of a circular lumen, using a balloon inflation index (BII).

In some embodiments, a processor (e.g., a processor of the ablation system) derives the disclosed change in one or more dimensions, and the BII, using measured changes in radial and/or longitudinal dimensions (e.g., radius, length, curvature) of the pressed balloon relative to the same balloon when inflated free of constraints. A balloon that is inflated in free space (i.e., inflated and unconstrained), such as in a blood pool of a chamber of the heart, has, by definition, a BII of 100%. A balloon inflated in a constrained space, such as inside a lumen (e.g., a pulmonary vein) has a reduced radius while its length increases. The changed dimensions of the balloon correspond to a smaller BII, as calculated below, and the smaller BII provides an indication of how well the circular ostium of the pulmonary vein is occluded.

In some embodiments the balloon is first inflated in a blood pool, and the processor measures the dimensions of the inflated balloon in free space for use as a reference (i.e., measures the dimensions of the inflated and unconstrained balloon). Then the balloon is inserted into the PV ostium, and the processor measures the dimensions of the constrained (e.g., pressed) balloon. The processor calculates the BII based on one or more measured changes in balloon dimensions.

Furthermore, the detection can be performed by (a) comparison of the known mechanical shape and dimensions of the fully inflated balloon, e.g., outside the body, vs. a real time visualization of the defoamed balloon before ablation, and/or (b) monitoring in real time rapid changes in the balloon shape and dimensions that can occur due to force an external force exerted on the balloon by the physician pushing the inflated balloon against the PV ostium to fully occlude the PV.

In other embodiments, a deflated, or partially inflated, balloon is first inserted into the lumen and only then the balloon is inflated to occlude the lumen. In such a case, the processor calculates the BII using known dimensions of the free space inflated balloon as compared with one or more measured dimensions of the pressed balloon.

As indicated above, a BII may be defined by various changes in dimensions of the balloon. For example, assuming the balloon has a radius $R_0$ and length $L_0$ when freely inflated and, as a result of the balloon being inflated inside an ostium, the balloon radius drops by 10% (i.e., $\Delta R = -0.1 R_0$), and while, at the same time, the balloon elongates by 10% (i.e., $\Delta L = 0.14$), an inflation index defined as $$BII1 = 100 \cdot \frac{1 + \Delta R/R_0}{1 + \Delta L/L_0},$$

drops from 100% to 82%. Such a BII type is defined by a change in shape of the balloon from spherical to prolate spheroid.

In some embodiments, the processor measures the change in radius using position signals received from electrodes, e.g., ablation electrodes) disposed over a membrane of the balloon. The processor measures the change in length using additional position signals received from one or more sensors disposed proximally and/or distally to the balloon on a shaft to which the balloon is coupled.

In other embodiments, for example if the position signals are available only from one or more electrodes disposed over the membrane of the balloon, such as from ablation electrodes, the processor can calculate only a change in the radius of the balloon with reasonable accuracy, for example, of an equatorial radius of the balloon. In such a case, a BII may be defined in a way that depends only on the radius. For example, using a respective change in balloon curvature k, $k=1/R$, $\Delta k = -\Delta R/R^2$, a radius-dependent BII2 is defined as $$BII2 = 100 \cdot \left(1 - \frac{\Delta k}{k}\right)^2,$$

where BII2 would drop from 100% to 81% when the balloon radius is reduced by 10%.

Based on the above comparison between BII1 or BII2 theoretical values, it may be sufficient to determine a degree of balloon occlusion solely using position signals from electrodes disposed over a membrane of the balloon. In practice, however, the accuracy of the measured positions of the balloon electrodes may be improved by using additional position signals, as described below. Therefore, the actual accuracy of BII1 may exceed that of BII2.

In an embodiment, the processor provides to a physician an indication of a degree of lumen occlusion in the form of a numerical grade comprising, for example, a BII value. In another embodiment, the processor outputs a textual indication that is based on the BII value, such as "Very Good" for a BII value between, for example, 75% and 84%, or "Insufficient" for a BII value between 95% and 100%, and so forth.

Typically, the processor is programmed in software containing a particular algorithm that enables the processor to conduct each of the processor-related steps and functions outlined above.

By providing an indication of a degree to which the ablation balloon occludes a lumen, for example through the disclosed BII value, the disclosed technique can improve accuracy of the balloon catheter positioning against lumen tissue and thereby improve effectiveness of balloon ablation. Furthermore, the disclosed technique, which does not require X-ray fluoroscopy imaging with use of contrast material, is safe for both patients and physicians.

The disclosed technique thus provides, in real time, a complete and safe assessment of individual balloon electrode contact with tissue, which may improve the outcome of cardiac balloon ablation treatments, such as of pulmonary vein (PV) isolation, as a treatment of arrhythmia.

System Description

FIG. 1 is a schematic, pictorial illustration of a catheter-based position-tracking and ablation system 20 comprising a radiofrequency (RF) ablation balloon 40, in accordance with an embodiment of the present invention. System 20 includes an Active Current Location (ACL) position tracking sub-system and, optionally, a magnetic position tracking sub-system. In some embodiments, system 20 is used for RF ablation of an ostium 51 of a PV (shown in inset 25) with balloon 40. The ACL sub-system is used to estimate a degree of inflation of balloon 40 after the balloon is inflated inside a lumen (e.g., an ostium), so as to ensure efficient subsequent balloon ablation.

Physician 30 navigates balloon 40 to a target lumen in a heart 26 of a patient 28 by manipulating a shaft 22 using a manipulator 32 near the proximal end of the catheter and/or deflection from a sheath 23. Balloon 40 is inserted, in a folded configuration, through sheath 23, and only after the balloon is retracted from sheath 23 does balloon catheter 40 regain its intended functional shape. By containing balloon catheter 40 in a folded configuration, sheath 23 also serves to minimize vascular trauma on its way to the target location.

To determine a degree of inflation of balloon 40, system 20 measures changes in one or more dimensions (e.g., radius and length) of balloon 40. To measure a change in dimension, a processor 41 of system 20 uses, at minimum, position signals from RF ablation electrodes 50 (seen in inset 25) of balloon 40, which function, for this purpose, as ACL sensing-electrodes.

Electrodes 50 are connected by wires running through shaft 22 to interface circuits 44 in a console 24 for receiving ACL signals. The ACL signals are measured relative to ACL surface electrodes 49, which are seen in the exemplified ACL system as attached by wires running through a cable 39 to the chest and to the back of patient 28. Console 24 drives a display 27, which shows the position and, optionally, the shape of balloon 40 inside heart 26.

The method of electrode position sensing using system 20 with ACL is implemented in various medical applications, for example in the CARTO™ system, produced by Biosense-Webster Inc. (Irvine, Calif.) and is described in detail in U.S. Pat. Nos. 7,756,576, 7,869,865, 7,848,787, and 8,456,182, whose disclosures are all incorporated herein by reference with a copy provided in the Appendix.

As noted above, a BII value may be derived using only position-indicative signals from electrodes 50. However, to improve accuracy, signals from additional position sensors, such as sensors disposed on shaft 22 in the vicinity of balloon 40, may also be used. A method to improve accuracy of position measurement using additional signals received from position sensors disposed on the distal end of the shaft, such as from electrodes fitted on the shaft of the catheter on either side of the balloon, is described in U.S. patent application Ser. No. 15/985,149, filed May 21, 2018, entitled "Scaling Impedance Location Measurements of a Balloon Catheter," which is assigned to the assignee of the present patent application and whose disclosure is incorporated herein by reference.

Additionally or alternatively, additional position signals from a magnetic position sensor fitted in the distal end of shaft 22 may be used. In some embodiments, console 24 further comprises a magnetic position-sensing sub-system. Patient 28 is placed in a magnetic field generated by a pad containing magnetic field generator coils 42, which are driven by unit 43. The magnetic fields generated by coils 42 generate direction signals in a magnetic sensor 38, which are then provided as corresponding electrical inputs to processor 41, which uses these to calculate a direction of the distal end of shaft 22 to which balloon 40 is fitted, thus correcting the positions derived using the ACL method.

The method of position sensing using external magnetic fields is implemented in various medical applications, for example, in the CARTO™ system, produced by Biosense Webster Inc., and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference with a copy provided in the Appendix.

As indicated above, in some embodiments, the balloon catheter further comprises a distal position sensor 55, that can be a magnetic sensor or a sensing electrode used by the ACL sub-system. Using additional position signals from sensor 55 in combination with signals from magnetic sensor 38 and/or electrodes 50, processor 41 can estimate a change in length of the balloon catheter by estimating a change in a longitudinal distance (i.e., parallel to the distal end of shaft 22) between positions measured by the various sensors.

Processor 41 is typically a general-purpose computer programmed in software to carry out the functions described herein. In particular, processor 41 runs a dedicated algorithm as disclosed herein, including that shown in FIG. 3, that enables processor 41 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description.

Identifying Pulmonary Vein Occlusion by Dimension Deformations of Balloon Catheter FIGS. 2A and 2B are schematic side-view illustrations of balloon 40 of FIG. 1 in free and constrained inflated states, respectively, in accordance with an embodiment of the present invention.

As seen in FIG. 2A, a balloon 40 inflated in free space resembles a sphere having an equator 45 about a longitudinal 66 axis that is parallel to the distal end of shaft 22. A length 61 is defined between a distal edge of the balloon, and a proximal end of the balloon.

Ablation electrodes 50 are seen disposed over a membrane 71 the balloon. Also seen are magnetic sensor 38 located just proximally to balloon 40 and a sensing-electrode 55, located just distally to the balloon. In some embodiments, a magnetic sensor replaces or is added to sensing-electrode 55.

FIG. 2B shown balloon 40 inflated to occlude ostium 51. As seen, due to the balloon being pressed against the walls of the ostium, the radius of the equator is reduced by a change 60 in the radius. Furthermore, the balloon is characterized by an increased length 62 along longitudinal axis 66 of the balloon, as the shape of the balloon comes to resemble a prolate spheroid.

Using the measured change (e.g., a decrease 60) in radius ΔR of an equator 45, and the measured change (e.g., an increase 64) in length, ΔL, from length 61 to length 62, processor 22 can derive a BII value using, for example, $$BII1 = 100 \cdot \frac{1 + \Delta R / R_0}{1 - \Delta L / L_0}.$$

where ΔR is the change in radius of the balloon; $R_0$ is the original radius of the unconstrained balloon; ΔL is the change in length of the balloon; and $L_0$ is the original length of the unconstrained balloon.

Figure 2:
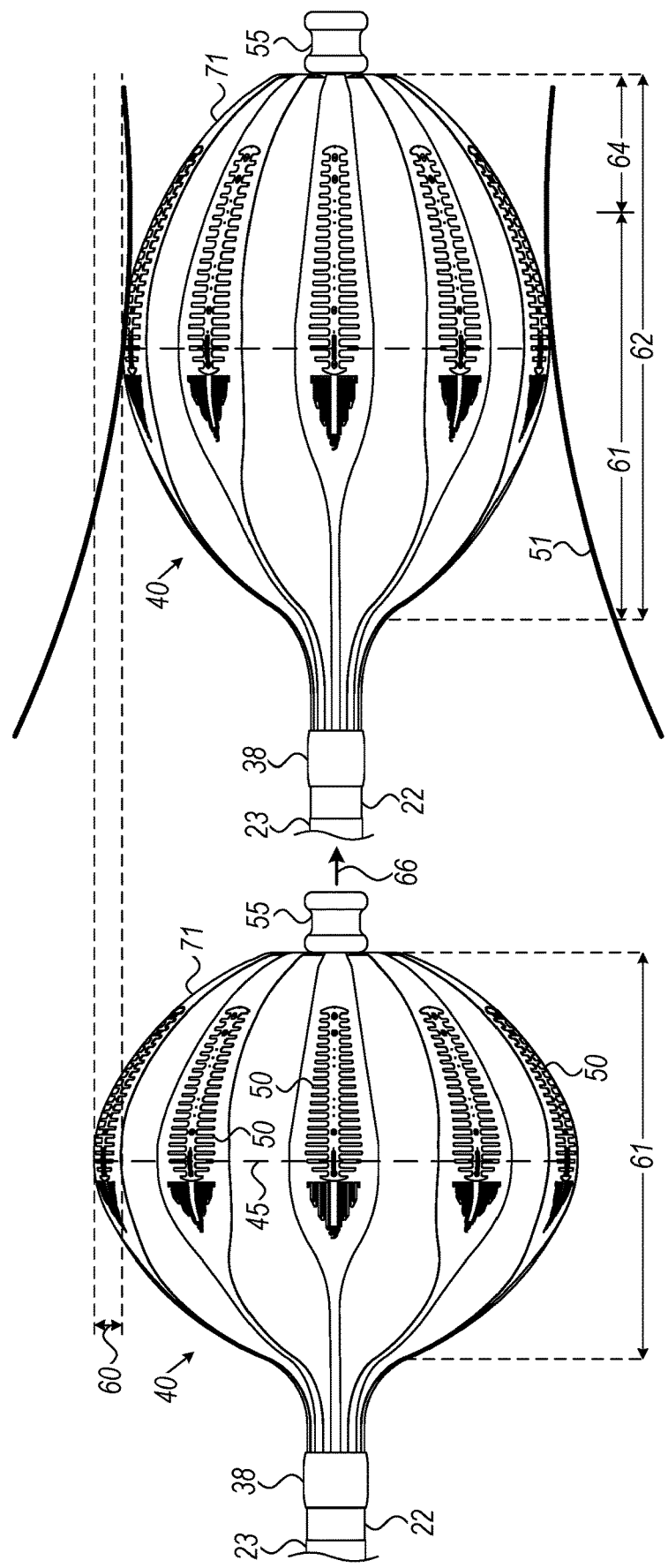
FIGS. 2A and 2B are schematic side-view illustrations of the balloon of FIG. 1 in free and constrained inflated states, respectively, in accordance with an embodiment of the present invention.

The illustration shown in FIG. 2 is chosen purely for the sake of conceptual clarity. Other geometries of ablation electrodes are possible. Elements which are not relevant to the disclosed embodiments of the invention, such as irrigation ports and temperature sensors, are omitted for the sake of clarity.

Figure 3:
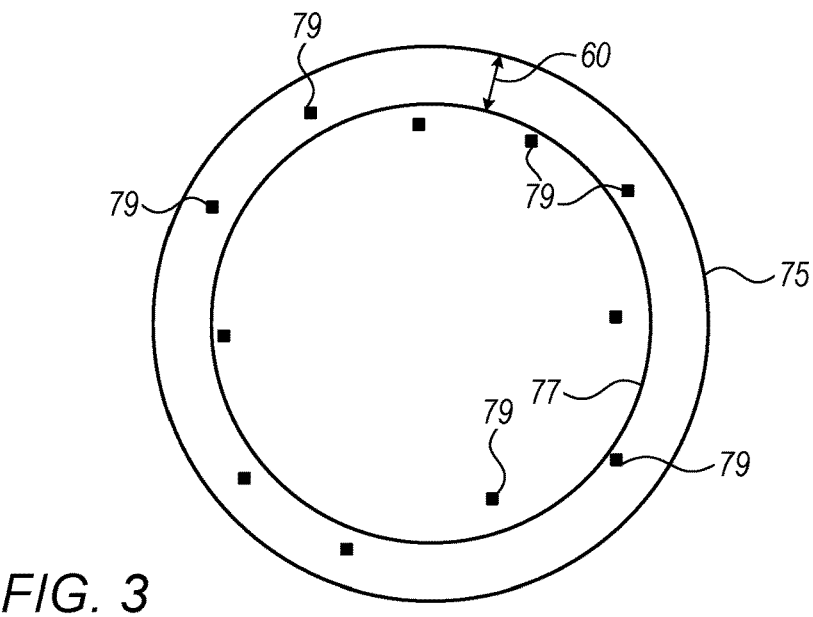
FIG. 3 is a plot that schematically illustrates a derivation of a change in the radius of the balloon of FIGS. 2A and 2B using Active Current Location (ACL) measurements, in accordance with an embodiment of the present invention.

FIG. 3 is a plot that schematically illustrates a derivation of a change in a radius of the balloon of FIGS. 2A and 2B using Active Current Location (ACL) measurements, in accordance with an embodiment of the present invention. Circle 75 represents equator 45 of the balloon inflated in free space, where equator 45 has a known radius, typically in the range of ten to fifteen millimeters, depending on the balloon model.

Radial positions 79 (FIG. 3) of electrode 50 are derived by processor 41 using ACL signals from ablation electrodes 50 and surface electrodes 49 (i.e., using the aforementioned ACL method). Using, for example, calibration, radial positions 79 represent approximately a circle on a plane defined by equator 45. To find a radial change 60, processor 41 fits a circle 77 to radial positions and calculates radial change 60 as the difference between the known radius of circle 75 and the radius of fitted circle 77.

Processor 41 then calculates a BII, for example, using $$BII2 = 100 \cdot \left(1 - \frac{\Delta k}{k}\right)^2,$$

where k, defined by k=1/R, is the respective curvature of the balloon, Δk, $\Delta k = -\Delta R/R^2$ is a respective change in balloon curvature calculated from radial change 60, ΔR, and using an average of radiuses 75 and 77, R.

BII2, which is derived solely using signals from ablation electrodes disposed over a membrane of balloon 40, may be sufficiently accurate to estimate a degree of occlusion. However, using additional position signals, such as from sensors 38 and/or 55 disposed on shaft 22 proximally and distally to balloon 40, respectively, may improve the accuracy of measured positions 79 and therefore the accuracy of BII2.

Figure 4:
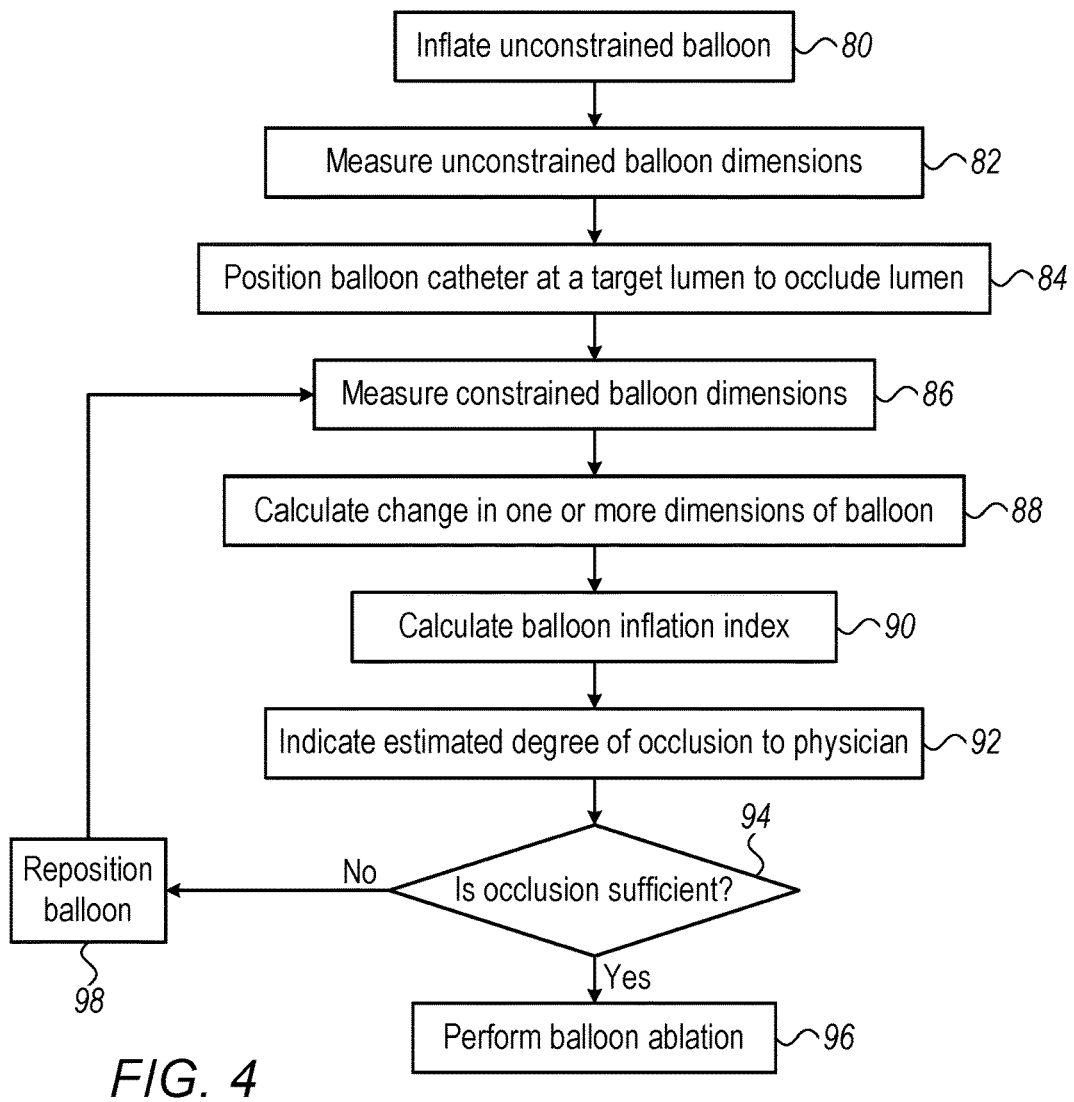
FIG. 4 is a flow chart that schematically illustrates a method and algorithm for estimating a degree of occlusion of an ostium by the balloon of FIG. 1, in accordance with an embodiment of the present invention.

FIG. 4 is a flow chart that schematically illustrates a method and algorithm for estimating a degree of occlusion of an ostium by balloon 40 of FIG. 1, in accordance with an embodiment of the present invention. The algorithm, according to the present embodiment, carries out a process that begins with physician 30 inflating the balloon unconstrained, e.g., in the blood pool within the heart, at a balloon inflation step 80. Next, at a first balloon measuring step 82, system 20 uses electrodes 50 and surface electrode 49 via ACL, magnetic or a hybrid ACL and magnetic location sensing technique to determine, i.e., to measure the unconstrained balloon dimensions, such as to determine a radius of the unconstrained balloon 40, e.g., of an equator 45 of unconstrained balloon 40.

Next, physician 30 positions balloon catheter 40 at a target location inside a lumen of heart 26, such as at an ostium of a pulmonary vein, at a balloon positioning step 84. At a constrained balloon measuring step 86, system 20 uses electrodes 50 and electrode 55 to measure a radius of pressed balloon 40, e.g., of an equator 45 of pressed balloon 40. Next, based on the measured equatorial radius of the freely inflated balloon 40, and, that of the pressed balloon, processor 41 calculates the change 60 in balloon equatorial radius, at a balloon dimensions change calculation step 88.

In an embodiment, processor 41 applies in step 88 the method described in FIG. 3 to derive radial change 60 (i.e., reduction in radius).

Next, using calculated change 60, processor 41 calculates a balloon inflation index (BII), such as BII2, at BII calculation step 90.

Based on the calculated balloon inflation index, system 20 indicates to physician 30 a degree of occlusion of the ostium, for example, by presenting a grade on display 27, at an occlusion indicating step 92.

Based on the grade, physician 30 decides if balloon 40 is positioned sufficiently well, relative to the ostium, at a decision step 94.

If physician 30 decides that balloon 40 occludes the ostium sufficiently well, then physician 30 performs a treatment, such as an RF ablation, in an RF balloon treatment step 96.

If, on the other hand, the physician 30 decides that balloon 40 does not occlude the ostium sufficiently, the process goes to a repositioning step 98, during which physician 30 attempts to better occlude the ostium. The process then loops to step 86 to remeasure constrained balloon constrained balloon dimensions and to re-estimate the degree of occlusion.

The example flow chart shown in FIG. 4 is chosen purely for the sake of conceptual clarity. The present embodiment also comprises additional steps of the algorithm, such as acquiring X-ray images, which have been omitted from the disclosure herein purposely on order to provide a more simplified flow chart. In addition, other steps, such as applying irrigation, are omitted for clarity of presentation.

Although the embodiments described herein mainly address cardiac applications, the methods and systems described herein can also be used in other applications, such as in otolaryngology, neurology, cardiology, blood vessel treatment and renal denervation.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving position signals that are indicative of positions of multiple electrodes disposed on an expandable balloon that is fitted at a distal end of a shaft for engaging a lumen of an organ to occlude the lumen;
   based on the received position signals, calculating a change in one or more dimensions of the balloon between (i) a first configuration in which the balloon is inflated but not engaged in the lumen, and (ii) a second configuration in which the balloon is inflated and engaged in the lumen;
   using the calculated change, deriving a Balloon Inflation Index (BII) indicative of an estimated degree to which the balloon occludes the lumen, the BII being based at least in part on a respective change in balloon curvature between the first configuration and the second configuration; and
   presenting the estimated degree of occlusion to a user.

2. The method according to claim 1, wherein the BII is derived by the following equation:
   $BII=100(1-(\Delta k/k))^2$ where k is a respective curvature of the balloon and $\Delta k$ is the respective change in balloon curvature between the first configuration and the second configuration.

3. The method according to claim 1, wherein calculating the change in dimensions comprises calculating a change in a radius of the balloon.

4. The method according to claim 3, wherein calculating the change in the radius of the balloon comprises:
   measuring positions of ablation electrodes disposed over the expandable balloon using Active Current Location (ACL);
   best fitting a circle to the measured positions; and
   calculating a radius of the best fitted circle.

5. The method according to claim 1, wherein receiving the position signals comprises receiving additional position signals from one or more position sensors disposed on the distal end of the shaft, and wherein calculating the change in dimensions comprises calculating a change in a length of the balloon along a longitudinal axis of the balloon based on the additional position signals.

6. The method according to claim 5, wherein the BIT is further derived by the following equation:
   $BII=100[(1+(\Delta R/R_0))/(1-(\Delta L/L_0))]$ where $\Delta R$ is a change in radius of the balloon, $R_0$ is a radius of the balloon in the first configuration, $\Delta L$ is the change in the length of the balloon, and $L_0$ is a length of the balloon in the first configuration.

7. The method according to claim 5, wherein the one or more position sensors are magnetic sensors.

8. The method according to claim 1, wherein estimating the degree to which the balloon occludes the lumen comprises numerically grading the degree.

9. The method according to claim 1, wherein estimating the degree to which the balloon occludes the lumen comprises textually grading the degree.

10. The method according to claim 1, wherein the lumen comprises an ostium of a pulmonary vein (PV).

11. A system, comprising:
    an interface, configured to receive position signals that are indicative of positions of multiple electrodes disposed on an expandable balloon that is fitted at a distal end of a shaft for engaging a lumen of an organ to occlude the lumen; and
    a processor, which is configured to:
    based on the received position signals, calculate a change in one or more dimensions of the balloon;
    using the calculated change in dimensions, derive a Balloon Inflation Index (BII) indicative of an estimated degree to which the balloon occludes the lumen, the BII being based at least in part on a respective change in balloon curvature between (i) a first configuration in which the balloon is inflated but not engaged in the lumen, and (ii) a second configuration in which the balloon is inflated and engaged in the lumen; and
    present the estimated degree of occlusion to a user.

12. The system according to claim 11, wherein the BII is derived by the following equation:
    $BII=100(1-(\Delta k/k))^2$ where k is a respective curvature of the balloon and $\Delta k$ is the respective change in balloon curvature between the first configuration and the second configuration.

13. The system according to claim 11, wherein the processor is configured to calculate the change in dimensions by calculating a change in a radius of the balloon.

14. The system according to claim 13, wherein the processor is configured to calculate the change in the radius of the balloon by:
    receiving measured positions of ablation electrodes disposed over the expandable balloon using Active Current Location (ACL);
    best fitting a circle to the measured positions; and
    calculating a radius of the best fitted circle.

15. The system according to claim 11, wherein the processor is configured to receive additional position signals from one or more position sensors disposed on the distal end of the shaft, and to calculate the change in dimensions by calculating a change in a length of the balloon along a longitudinal axis of the balloon based on the additional position signals.

16. The system according to claim 15, wherein the BIT is further derived by the following equation:
    $BII=100[(1+(\Delta R/R_0))/(1-(\Delta L/L_0))]$ where $\Delta R$ is a change in radius of the balloon, $R_0$ is a radius of the balloon in the first configuration, $\Delta L$ is the change in the length of the balloon, and $L_0$ is a length of the balloon in the first configuration.

17. The system according to claim 15, wherein the one or more position sensors are magnetic sensors.

18. The system according to claim 11, wherein the processor is configured to estimate the degree to which the balloon occludes the lumen by numerically grading the degree.

19. The system according to claim 11, wherein the processor is configured to estimate the degree to which the balloon occludes the lumen by textually grading the degree.

20. The system according to claim 11, wherein the lumen comprises an ostium of a pulmonary vein (PV).

* * * * *